United States Patent [19]
Idriss

[11] Patent Number: 4,931,050
[45] Date of Patent: Jun. 5, 1990

[54] CONSTANT PRESSURE VARIABLE FLOW PUMP

[75] Inventor: Samir F. Idriss, Mattapan, Mass.

[73] Assignee: Shiley Infusaid Inc., Norwood, Mass.

[21] Appl. No.: 180,916

[22] Filed: Apr. 13, 1988

[51] Int. Cl.⁵ ............................................. A61M 31/00
[52] U.S. Cl. ................................ 604/891.1; 604/141; 604/246; 128/DIG. 12
[58] Field of Search ................. 604/65, 93, 131, 132, 604/134, 135, 140, 141, 151, 175, 246, 247, 890.1, 891.1, 153, 249; 128/DIG. 12; 137/803; 138/46

[56] References Cited

U.S. PATENT DOCUMENTS

| | | | |
|---|---|---|---|
| 3,557,833 | 1/1971 | Gilmont | 138/46 |
| 3,951,147 | 4/1976 | Tucker et al. | 604/891.1 |
| 4,221,219 | 9/1980 | Tucker | 604/141 |
| 4,258,711 | 3/1981 | Tucker et al. | 604/175 |
| 4,443,218 | 4/1984 | DeCant, Jr. et al. | 128/DIG. 12 |
| 4,487,603 | 12/1984 | Harris | 128/DIG. 12 |
| 4,496,343 | 1/1985 | Prosl et al. | 604/141 |
| 4,541,429 | 9/9185 | Prosl et al. | 604/249 |
| 4,626,244 | 1/1986 | Reinicke | 604/141 |
| 4,668,231 | 5/1987 | de Vries et al. | 604/891.1 |
| 4,692,146 | 9/1987 | Hilger | 604/890.1 |
| 4,699,615 | 10/1987 | Fischell et al. | 604/153 |
| 4,705,501 | 11/1987 | Wigness et al. | 604/175 |
| 4,714,462 | 12/1987 | DiDomenico | 604/891.1 |
| 4,718,893 | 1/1988 | Dorman et al. | 604/151 |
| 4,772,263 | 9/1988 | Dorman et al. | 604/891.1 |
| 4,798,207 | 1/1989 | Wade | 604/175 |
| 4,813,951 | 3/1989 | Cannon | 604/891.1 |
| 4,838,887 | 6/1989 | Idriss | 604/246 |

Primary Examiner—Stephen C. Pellegrino
Assistant Examiner—Ralph Lewis
Attorney, Agent, or Firm—Sughrue, Mion, Zinn, Macpeak & Seas

[57] ABSTRACT

A variable flow constant pressure implantable pump employs an in-line needle restrictor having a variable insertion distance in a capillary. The degree of insertion determines the effective restriction within the capillary. The restrictor may be repositioned following implantation to vary the drug delivery rate by changing the effective restriction in the capillary. Various couplings may be used such that an auxiliary or bolus port delivers infusate directly into the outlet catheter so that medication from the main chamber does not pass through the auxiliary chamber. A combination of double lumen catheters and T-connectors are employed to provide parallel infusion paths.

11 Claims, 4 Drawing Sheets

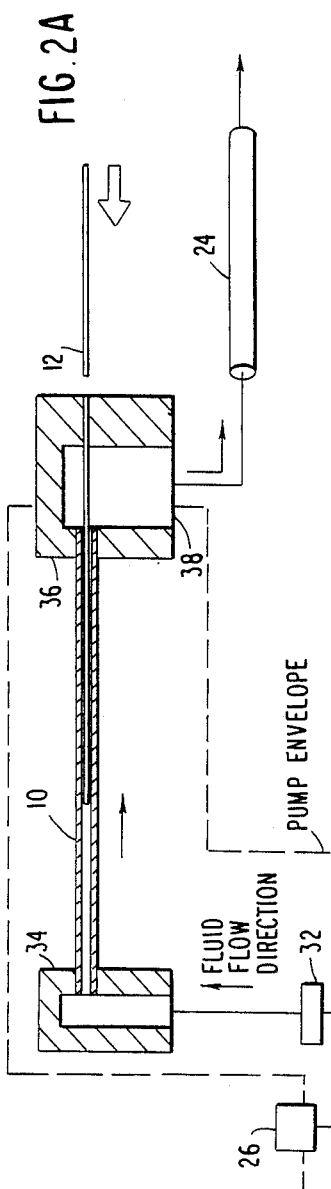
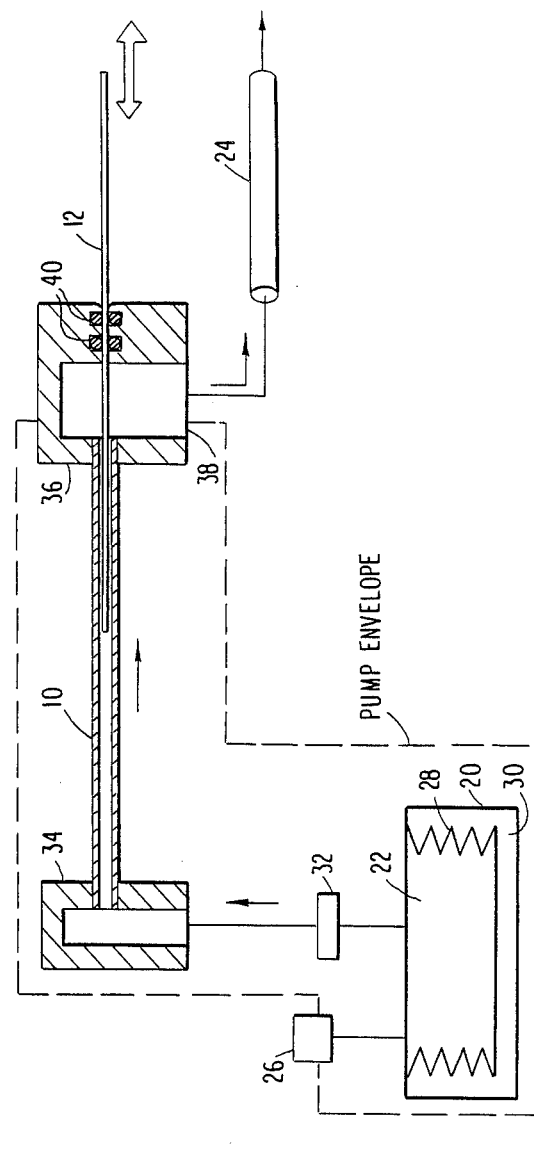

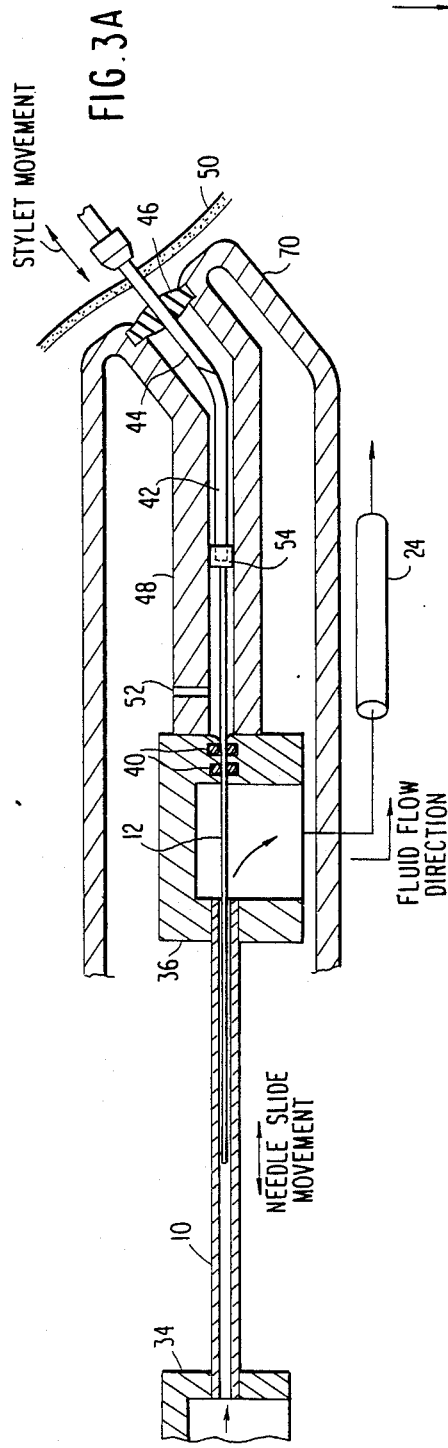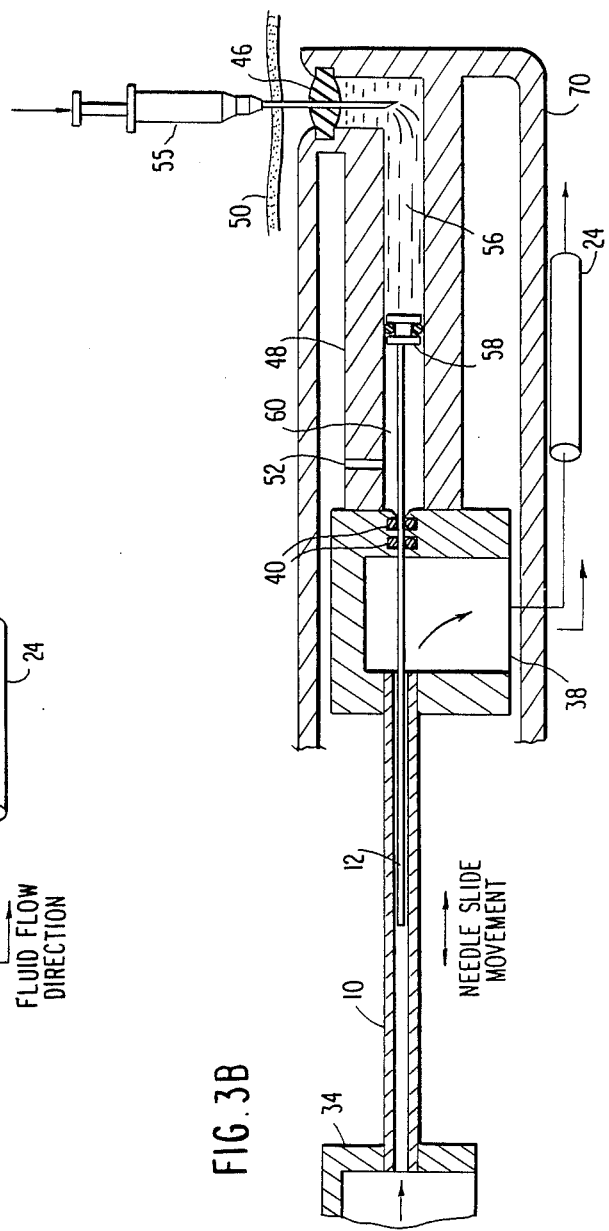

CONSTANT PRESSURE VARIABLE FLOW PUMP

BACKGROUND OF THE INVENTION

This invention relates to an implantable infusion pump. In particular, it relates to an infusion system utilizing a rechargeable, implantable constant pressure pump together with unique catheter arrangements to provide variable infusion rates.

Infusion pumps that are implanted in the body for delivery of an infusate, typically a medication or insulin to a selected site in the living body have reached the point of commercial and medical acceptance. Those devices generally fall into two categories. The first, are so-called constant flow devices which are used in a variety of medical applications, for example, to dispense chemotherapy drugs at a relatively constant flow rate. The technology represented by such constant flow devices is found in U.S. Pat. Nos. 3,731,681; 4,193,397; and 4,258,711. Those patents are representative of a number of other patented technology wherein an infusion apparatus relies on a liquid/vapor equilibrium to maintain constant pressure on the drug which flows through a capillary in order to maintain a constant flow rate. The device is implanted in the body to remain there for a prolonged period and is refilled with an infusate without the need for removal. Refilling is achieved by injecting additional infusate through a penetrable septum in the apparatus. The septum is located directly under the patient's skin and is sensed by tactile location. During the act of refilling of the apparatus with infusate, recharging of the apparatus' power supply also takes place since the liquid/vapor equilibrium is shifted by an increase in pressure in the infusate chamber.

A second class of devices are the so-called "programmable" devices which employ a valve or other device controlled by a programmer so that the dosage rate can be varied to suit the needs of a particular patient. An example is diabetes, where the quantity of medication, such as insulin, to be infused varies as a function of the requirements of the patient. Such fluctuations can occur on a daily basis or, randomly as a function of the ingestion of food. The patient receives a small continuous or basal dose to satisfy a particular steady state requirement as a function of the average amount of sugar in his blood following eating, when blood sugar levels rise dramatically, the infusion apparatus is programmed to dispense a larger (bolus) dose of insulin to offset the increased sugar level caused by the ingestion of a meal. The technology represented by such programmable devices is represented in U.S. Pat. Nos. 4,077,405; 4,443,218; 4,447,224; and 4,714,462.

While basic constant flow devices offer simplicity in operation and design, they do not allow for flexibility in dosage which is required by a number of treatment regimes. Conversely, while programmable pumps provide such flexibility, they suffer from difficulties in the areas of power consumption, overall life, and failsafe operation.

In order to address these two concerns, U.S. Pat. No. 4,496,343 relies on a constant pressure implantable infusion pump having attached to it an auxiliary chamber used for unrestricted bolus injections of medication and other fluids through the pump's infusion line, generally a catheter, to the delivery site. This auxiliary chamber or "bolus port" contains its own self-sealing septum which is accessed percutaneously via a hollow needle puncture. The auxiliary chamber is serially connected to the reservoir and, whether mounted internal or external to the pump, fluid flowing through the main reservoir passes through this auxiliary chamber prior to exiting through the delivery catheter.

Another alternative to programmable systems is found in U.S. Pat. No. 4,258,711. The system described therein employs two parallel reservoirs, each separately rechargeable and delivering via parallel flow paths a constant basal dosage or, a manual bolus. The bolus dose is held in an accumulator which is manually released by means of a button located externally which actuates an internally placed valve so that in addition to the constant flow basal dose, a "one-shot" bolus dose is delivered from the accumulator. While this system eliminates the complexities inherent in electronics which require an explant for changes of power source, nevertheless, the overall implantable system remains complex with bolus dose dependent on actuation of a manual valve coupled with multiple reservoirs. From the foregoing, it can be appreciated that the technology is advancing in an attempt to provide the necessary flexibility for varying drug delivery dosages without unnecessarily encumbering such systems with complex devices which increase the propensity for failure. Moreover, the utility of an auxiliary port has been demonstrated by commercial devices such as the Infusaid Model 400 to perform bolus injections, and to provide the ability to maintain catheter patency by periodic or high-pressure flushing. Additionally, such auxiliary ports provide additional flexibility with respect to the extraction of fluid samples such as blood from the delivery site. Such flexibility is inherent in a system which utilizes a single bolus port but cannot be accomplished in a system that employs valve technology such as the '711 patent.

One characteristic of utilizing a relatively unobstructed, serial catheter access device is that a bolus injection will force the infusate stored in the chamber through the catheter as the chamber volume is flushed. While such a characteristic is present in systems designed by the '343 patent, as noted, for certain drug therapy such as insulin, the therapy regime cannot tolerate a bolus drug injection per se and thus, a different flow configuration must be pursued which allows the use of an auxiliary port without the hazards of chamber flushing. Additionally, while the extraction of blood from the delivery site is desirable from a diagnostic standpoint, such may cause a build-up of blood products on the internal, relatively small, passages of the capillary tubing in '343. This in turn may lead to clotting and the blockage of flow. Obviously, alternative configurations are required.

Capillary tube restrictors which are used in such implantable devices have the advantage of providing a simple and low cost fluid restriction. Generally, large internal diameters (0.003-0.004 inches) are coupled with long lengths (sometimes in excess of thirty feet wrapped around the implantable device) to provide the necessary restrictions with reduced risk of contamination due to plugging and a large degree of freedom insofar as trimming to a desired flow rate. The overall length and the internal diameter are chosen to provide low shear rate, laminar flow in order to reduce the stress on a specific drug solution which may be sensitive to shear. However, such long lengths of capillary tubing increase the space requirement and overall weight of the system. In the context of an implantable device, these two properties are significant drawbacks in that they limit areas where implantation may occur and provide a degree of user discomfort. Moreover, the actual measuring, calibration and trimming of long tube lengths is labor intensive and requires a considerable amount of time.

U.S. Pat. No. 3,951,147 relating to an implantable infusate device describes a technique for replacing the long length of catheter tubing by employing a flow controller utilizing a large bore diameter tubing having placed therein a resistance wire. By properly sizing the diameter and length of the resistance wire, flow control can be maintained. The '147 patent therefore proceeds by reducing the overall length of the capillary tubing through the use of a shorter tubing having placed therein a predetermined length of wire to achieve the necessary flow characteristics of the overall device. However, no provision is made for extending the resistance wire external to the capillary for adjustment during manufacture or adjustment during use (i.e. in-vivo).

SUMMARY OF THE INVENTION

Given the shortcomings of the prior art, it is an object of this invention to define a constant pressure variable flow infusion device that reduces space and overall weight of the system, lowers cost and allows external restriction trim.

Yet another object of this invention is to provide for a flow restriction system that provides relatively low shear rates in the context of a constant pressure variable flow device.

Still another object of this invention is to provide a variable flow device which allows for flow rate readjustment following implant, an advantage not possible in capillary tube restrictor technology.

A further object of this invention is to define a flow connection system that employs an auxiliary bolus port and its associated flow connections that does not require that infusate from the main reservoir pass through the bolus injection chamber to allow for flexibility in either direct bolus injection or the use of the auxiliary port for in-situ sampling.

These and other objects of this invention are accomplished by the use of a constant pressure delivery system given a refill septum and a main reservoir chamber. Infusate from the main reservoir chamber is delivered to the system utilizing a liquid/vapor equilibrium in the device to maintain constant pressure on the drug which then flows through an outlet capillary at an initial constant rate. In accordance with one aspect of this invention, a needle restrictor is placed in the capillary tube having a variable insertion distance. By utilizing various techniques external to the capillary, the needle restrictor may have its effective length in the capillary changed to thereby vary the effective restriction within the capillary and thus determine flow rate. To change flow rates of the constant pressure device, the needle restrictor's length is varied, for example, by shortening the effective length to decrease the resistance and increase the dosage or conversely, to increase the effective length and decrease the dosage. Varying techniques are employed to move the restrictor needle. For example, fluid cylinder actuated by means of external pressure, lead screw adjustment techniques, linear stylet techniques and the like may by employed. If serial bolus delivery is to be employed, a T-connector can be used to couple the fluid output from the main reservoir chamber such that the auxiliary or bolus port delivers infusate directly into the outlet catheter. By this technique, medication from the main reservoir chamber does not pass through the auxiliary chamber. Alternatively, a double lumen catheter may be used having one lumen receiving the output from the main reservoir chamber and the second receiving output from the bolus port. Such provides for parallel output. Alternatively, a combination of parallel output utilizing a double lumen catheter and serial output utilizing a second bolus port in a T-connection in the infusion path may be employed.

These and other aspects of the invention will be described in detail by referring to the attached drawings and the description of the preferred embodiments that follows.

BRIEF DESCRIPTION OF THE DRAWINGS

FIGS. 2A and 2B illustrate a first embodiment of this invention utilizing a linearly trimmed and fixed needle restrictor in an infusate system;

FIGS. 3A, 3B and 3C illustrate a second embodiment of an adjustable implanted variable flow system used in conjunction with a constant pressure drug delivery device;

FIGS. 4A, 4B and 4C illustrate a third embodiment of this invention utilizing a serial, parallel and hybrid serial/parallel bolus port system.

DESCRIPTION OF THE PREFERRED EMBODIMENTS

Figure 1A:
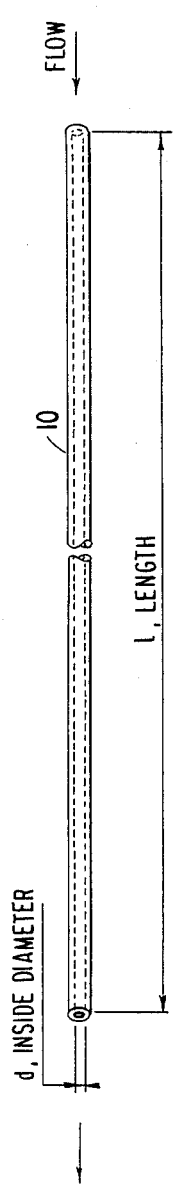
FIG. 1A is a schematic perspective drawing illustrating a capillary tube used in accordance with this invention.
Figure 1B:
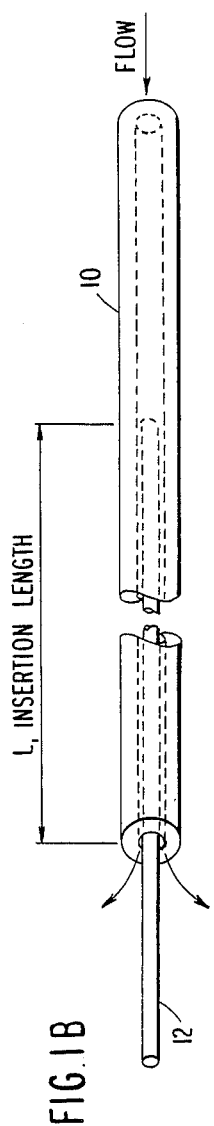
FIG. 1B is a schematic side view illustrating a capillary tube having an adjustable needle restrictor.
Figure 1C:
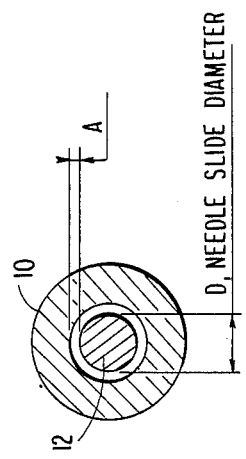
FIG. 1C is an end view of the capillary and restrictor of FIG. 1B.

Referring now to FIGS. 1A-1C, the basic flow principles of an adjustable needle restrictor used in combination with a capillary tube will be discussed. The capillary flow restrictor in accordance with this invention comprises an outer capillary tube 10 having a given length (1) and an inside diameter (d). A needle slide 12 is placed into the capillary tube 10. The needle slide 12 has a diameter (D) and is inserted for a variable insertion length (L). As illustrated in FIG. 1C, a radial clearance gap (A) exists which is equal to ½ of the diametrical clearance such that the needle slide diameter (D) is very much greater than the gap (A). Thus, in accordance with this first aspect of the invention, the variable flow capillary tube restrictor is a 2-part device comprised of a housing, that is the capillary tube and a needle slide. The capillary tube is essentially a smooth bore, semi-rigid tube into which the needle slide is positioned. The outer diameter of a needle slide (D) is also smooth and of a dimension which significantly matches the inside diameter (d) of the tube. Thus, a very narrow diametrical clearance (A) exists between the housing inside surface and the needle outside surface. It is this narrow passage in a portion of the tube 10 which acts as a flow restrictor for the fluid.

The relative length of insertion (L) of the needle slide in the housing determines the resistance, that is the actual restriction. The valve is linearly proportional to the length of insertion. A comparison of flow rate through a capillary tube and flow rate through the narrow restrictor of this invention can be described by reference to the following three equations:

$$QC = \text{Flow Rate Through} = \delta P d^4 \pi / 128 \mu l \quad (1)$$
$$\phantom{QC = }\text{Capillary Tube}$$

$$QN = \text{Flow Rate Through} = \delta P A^3 (D + A) \pi / 12 \mu L \quad (2)$$
$$\phantom{QN = }\text{Needle Restrictor}$$

$$\text{Hydraulic Resistance} = \delta P / \text{Flow Rate} \quad (3)$$

where:
 $\delta P$ = pressure differential across the restrictor
 $\mu$ = the absolute fluid viscosity
 $\pi$ = 3.14159 and
 d, l, D, A and L are as defined above.

As can be seen from the three equations and the basic assumption that D and d are much greater than A, the inside diameter of the housing is large enough so that its hydraulic resistance is much less than that of the slide-to-housing clearance gap and is therefore negligibly restrictive with respect to this gap.

The function of the restriction in the device is therefore the length of the flow gap (L) caused by the relative insertion position of the needle slide 12 in the capillary 10. The greater the length of the insertion, the greater the fluid restriction as defined by equation 2. This should be contrasted with the capillary tube restrictor per se which is a single element device with a fixed inside diameter and a trimmable length. Its flow restriction is fixed and determined solely by the inside diameter of the tube length. Consequently, as set forth in Equation 1 the restriction is set by having a fluid flow through the tube, measuring the flow rate, recutting the length of the tube in the amount proportional to the flow rate change and then reflowing to verify the new rate. Once cut, the flow rate cannot be readjusted back to the old values. Similarly, when the needle has been trimmed and fixed in the case of the prior art '147 patent, no capability exists for further adjustability.

This invention therefore departs from those prior art schemes by allowing the needle restrictor flow geometries to be altered by changing the insertion distance of the needle. By the proper choice of materials for the needle slide and housing, the elements maintain their relative positions during use. Alternatively, the relative positions of the needle and the housing can be maintained by utilizing arcuate shapes such that the needle slide is frictionally locked into the housing by the spring tension of the slide to the housing inside diameter.

Referring now to FIGS. 2A and 2B, a first embodiment of this invention will be described. FIG. 2A illustrates in schematic form the system which is insertable into a body cavity. The casing which forms the overall housing is illustrated by dashed lines to show those elements so packaged. A storage chamber 20 comprises a positive pressure drug reservoir in accordance with this invention. This device will be similar to the drug reservoir in a commercially available unit such as an Infusaid Model 100 or, Model 400, both manufactured by Shiley Infusaid, Inc. The device will be discussed herein only for an appreciation of the invention, it being understood that a commercially available component may be used. The storage chamber 20 comprises a housing which contains infusate in a reservoir 22. The path of fluid communication established between the chamber 22 and a delivery catheter 24 is illustrated by the arrows in FIG. 2A. This is the "forward flow" direction from the storage chamber to the infusion site.

In accordance with known principles, when infusate within housing 22 is exhausted, it may be refilled by subcutaneous injection through a self-sealing septum 26. Thus, when the device is properly implanted, the septum 26 is located directly beneath the patient's skin and accessible via syringe. The device 20 contains a bellows 28 which divides the device into two chambers, a first chamber 22 containing infusate and a second chamber 30, which is used to drive the bellows in accordance with the fluid/vapor equilibrium maintained utilizing Freon or the like.

The outlet path includes a bacterial filter 32 and a rigid reservoir attachment 34. The attachment 34 serves as a coupling between the pump interior and the housing 10 into which the needle slide 12 is inserted. At a point exterior to the pump, an outlet bulkhead attachment 36 is placed so that a rigid fixed length of housing 10 exists between the rigid reservoir attachment 34 and the outlet bulkhead attachment 36. The outlet bulkhead attachment 36 has a coupling chamber 38 to which the delivery catheter 24 is attached. It will be appreciated that the illustration in FIG. 2A is highly schematic to merely show the position of the elements. The actual device would be packaged much like current Infusaid models to have suture tie downs, minimum bulk and septum access. The needle restrictor housing 10 is relatively rigid while the delivery catheter 24 may be highly flexible to allow positioning within a body cavity to the infusate site.

In accordance with this invention, the needle slide 12 is inserted through the outlet bulkhead attachment 36 into the housing 10 until the desired flow rate is achieved. By this technique, with the pump 20 charged and an outlet produced through the needle restrictor housing 10, a flow rate can be positively monitored and dynamically adjusted. When that operation is completed, the needle slide 12 may be trimmed and sealed to the outlet bulkhead attachment.

FIG. 2B, carrying the same designation of common elements of FIG. 2A, illustrates a variation of this embodiment. In FIG. 2B, the restrictor 10 is attached to the pump housing via a seal packing 40. The packing may be a series of annular O-rings placed in compression within the outlet bulkhead attachment 36. This packing provides a sealed interface between the fluid flow path and the pump exterior. The seal allows repositioning of the insertion needle 12 for a simplified setting of flow restriction during manufacture or possible reset during use.

As illustrated in FIG. 2B, the seal packing 40 is located at the downstream end of the flow restrictor. That is, it is placed in a position downstream of the fluid flow from the housing 10 through the bulkhead 36 into the catheter 24. Such was important from a product safety standpoint because the failure of the sealed packing would not permit unrestricted "dumping" of the reservoir. Additionally, placing the seal distal to the restrictor means that fluid volume displaced during repositioning would be displaced into the reservoir and not to the infusion site, that is movement of the needle slide will not vary the infusate dose. In accordance with this embodiment, the needle slide may be repositioned after initial setting therefore providing variable flow rate setting of the pump during actual use. That is, in-vivo adjustment may be obtained after implantation.

FIGS. 3A, 3B and 3C illustrates three configurations to permit such repositioning of the flow restriction and therefore flow rate during in-vivo use of the system. In these embodiments, the exterior of the pump housing is illustrated, in part, as element 70. Thus, it will be understood that the reservoir attachment 34, the fixed needle restrictor housing 10, and the outlet bulkhead attachment 36 are all contained within the pump housing. The delivery catheter 24 would, however, be external to that housing. As in the prior illustrations, it will be appreciated that his drawing is schematic to emphasize the aspects of the invention. FIG. 3A illustrates a technique of percutaneously readjusting the restrictor 12 by employing a wire stylet through a large bore needle 44. The stylet 42 and large bore needle 44 can be placed in a self-sealing septum used for flow rate reset or a bolus septum similar to that disclosed in U.S. Pat. No. 4,496,343. Thus, attached to the outlet bulkhead attachment 36 is a penetrable septum 46 placed below the skin surface illustrated schematically as skin layer 50. The housing 48 holding the septum 46 in place has a vent 52 to provide for pressure relief as a function of sliding movement of the stylet 42. The stylet 42 is coupled to the needle slide 12 via a sliding threaded coupling 54.

One technique of accurately setting the restrictor position would be to push the needle 12 to its maximum restriction position, that is maximum insertion by stylet movement and then to "back" the needle out to a specific, precalibrated length to achieve the calibrated flow rate. The needle slide would be held in position by frictional contact with both the packing sealing 40 and the threaded coupling 54.

Referring to FIG. 3B, a variation of this embodiment is illustrated. As in the case of prior embodiments, the same numerals are used to identify common elements. FIG. 3B illustrates a configuration employing a fluid cylinder/actuator used to provide restrictor repositioning. The self-sealing septum 46 is punctured via a syringe 55 and a fluid contained in the syringe is injected to push the restrictor to its maximum closed position as illustrated by the arrows in FIG. 3B. The fluid is illustrated schematically as element 56 within the chamber 48 with a sealed piston actuator 58 used to maintain an air-tight interface between the entrained air in zone 60 on one side of the piston and the fluid 56 on the other side of the piston 58. Given an equilibrium condition which is maintained, a predetermined amount of fluid is then withdrawn utilizing the syringe 55 to set the restrictor to its desired flow position. The pressure differential across the piston actuator 58 therefore causes that actuator to move to the right in FIG. 3B, repositioning the slide needle 12 to the desired position and therefore to the desired flow rate.

Alternatively, fluid pressure in pushing against a spring loaded cylinder could be used to set the restrictor position.

FIG. 3C illustrates yet another variation employing a mechanical configuration to allow readjustment of the flow restriction following implant. Positioned on the housing is a rotating seal 72 which is maintained in a fluid-tight relationship by means of O-ring 74 and the like. The needle slide 12 has one end coupled to the lead nut coupling 76. That lead nut coupling is mounted on a lead screw 78. Through a large bore needle 80 is inserted a stylet 84 which has on one end, external to the skin, a shaped tip, for example, a hexagonal head, Phillips head, or the like and on the other end, a rotating knob 82. The shaped tip terminal end of the stylet 84 seats in the rotating seal 72.

As illustrated in FIG. 3C, one end of the lead screw 78 is also fixed to the rotating seal 72. Thus, as the knob 82 is rotated, a corresponding rotation is imparted via the stylet 84, rotating seal 72, and lead screw 78. The lead nut coupling being threaded on the lead screw therefore causes movement of the needle slide depending on the direction of rotation of the knob 82.

Alternatively, a small incision could be made to provide access to the adjustment screw instead of the large bore needle. While practically this might be desirable, it could not be used as frequently to adjust flow rates.

As pointed out herein, in accordance with this aspect of the invention, a replacement for the capillary tube restrictor in the context of a constant flow rate implantable infusion device has been described. By utilizing these embodiments, it is possible to realize significant advantages by reducing labor and cost to manufacture and significantly reduce the lead time for procurement. Additionally, each device can be configured to allow for readjustment of the flow restriction and thus flow rate after implant utilizing procedures which do not disturb the in-vivo nature of the device. Such is not possible with a capillary tube restrictor which offers only a single opportunity for calibration prior to implant.

Figure 4B:
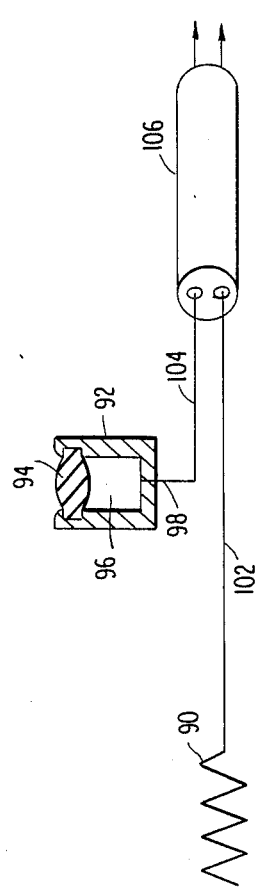
Figure 4C:
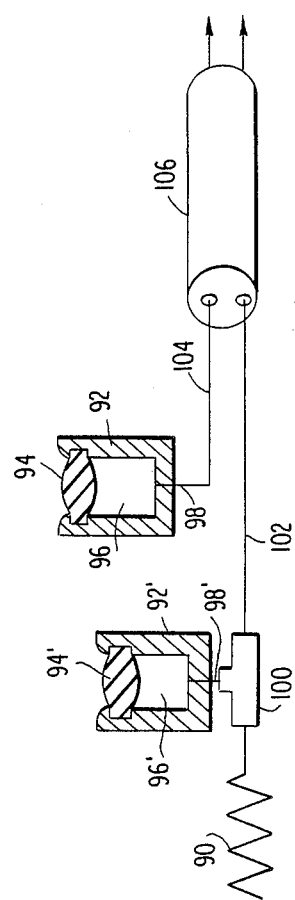

Referring now to FIGS. 4A, 4B, and 4C, a second aspect of this invention is depicted. Those elements common to the descriptions in FIGS. 2 and 3 contain the same numerals. Thus, for example, the constant pressure reservoir, refill septum, bacterial filter and the like are all provided with common numerals. A flow restrictor of the type illustrated in FIGS. 2 and 3 is schematically illustrated as the restriction 90. FIGS. 4A, 4B, and 4C illustrate three different configurations for attachment of an auxiliary chamber or "bolus port" 92 to an infusion pump flow system. Such a bolus port comprises a self-sealing septum 94, a chamber 96, and an outlet 98. Such an auxiliary bolus chamber is described per se in U.S. Pat. No. 4,496,343.

FIG. 4A illustrates a configuration providing the bolus port 92 plumbed in a spur line fashion utilizing a T-connector 100. In this configuration, the auxiliary chamber 96 is filled with a non-reactive solution such as a drug diluent. Normal flow occurs past the chamber via the output line 102 from the main reservoir chamber 22 to the outlet catheter 24. Thus, a drug is not stored in the chamber 96. When a bolus injection is performed, the only drug solution which is washed into the body is that which is contained in the catheter line downstream of the port 92. That is, the only residual drug solution which is forced through the catheter is that which exists from the T-connector 100 through the outlet of the catheter 24. This volume is relatively small with respect to the chamber volume and thus the effects are much less severe than in past techniques. The flow path illustrated in FIG. 4A would still allow for catheter maintenance through the port 92 and such techniques, for example, withdrawal of blood, could therefore be employed for diagnostic purposes at the infusion site.

FIG. 4B illustrates a second flow configuration specifically designed for blood withdrawal. In this configuration, the flow port is completely separate from the drug infusion line. This configuration employs a parallel set of infusion lines, the drug delivery line along conduit 102 and a separate line 104 providing two outlets to the double lumen catheter 106. The port 92 thus provides the capability of bolus injection as well as fluid withdrawal at the delivery site. This can be accomplished without in any way interrupting the flow of fluids from the main reservoir chamber 22 through the other lumen of the double lumen catheter 106. One advantage of this embodiment is the ability to design a port free of small internal flow passages much in the way vascular access ports are now configured. This technique, however, does not allow for complete catheter maintenance through the port since it is impossible to clear the lumen 102 in the double lumen catheter 106. In FIG. 4C, an additional port 92 (having the same numerals as that of port 92 but "primed") is added to the system of FIG. 4B. This additional port may be used specifically for catheter maintenance along line 102 and still be maintained separate from the blood/fluid withdrawal line 104 by the use of the double lumen catheter.

It can therefore be appreciated that in this aspect of the invention, by utilizing a proper combination of auxiliary ports; catheter maintenance, fluid withdrawal and separate aligned flushing can be accomplished when used in conjunction with flow restrictor technology as in the case of the other aspect of this invention.

It would be appreciated that this invention is subject to other modifications and variations without departing from the essential scope thereof.

Having described my invention, I claim:

1. An infusion system implantable in the living body comprising:
    a constant pressure reservoir for releasing fluid, an outlet conduit connectable to said reservoir,
    a flow restriction element inserted into said conduit, said flow restriction element having an axial insertion length (L) of penetration in said conduit and,
    means to vary the axial insertion length (L) of said flow restriction element from a point distant from an implantation site following implantation of said system wherein flow rate characteristics of said outlet conduit are adjusted so that the delivery rate of fluid from said reservoir is altered.

2. The infusion system of claim 1, further comprising:
    a delivery catheter, means to attach in fluid communication said outlet conduit to an end of said catheter, said flow restriction element having one end passing through said means to attach into said outlet conduit and having a second end external to said means to attach.

3. The infusion system of claim 2, wherein said means to vary the axial length of said flow restriction element is connected to said second end of said flow restriction element and said means to vary the axial length of said flow restriction element is placed in an adjustment conduit attached to said outlet conduit at one end and sealed on the other end by a penetrable septum.

4. The infusion system of claim 3, wherein said means to vary the axial insertion length of said flow restriction element comprises a flexible stylet, said stylet having one end coupled to said second end of said flow restriction element and having another end connected to a linearly movable element disposed external to an implantation site when said system is implanted in a living body.

5. The infusion system of claim 4, wherein said stylet passes through an insertion needle that penetrates, said septum into said adjustment conduit.

6. The infusion system of claim 3, wherein said adjustment conduit defines a fluid cylinder, said means to vary the axial insertion length comprises a sealed piston actuator coupled to said second end of said flow restriction element, and a syringe penetrable to an implantation site through said self-sealing septum, said syringe delivering or removing fluid from said fluid cylinder whereby in response to a pressure differential across said piston actuator said piston coupled to said flow restriction element moves until an equilibrium position is reached thereby varying the axial insertion length (L) of said flow restriction element in said outlet conduit.

7. The infusion system of claim 2, further comprising a housing for said reservoir, a seal mounted on said housing and rotatable, a lead screw coupled to said seal on one side for rotation therewith, a lead nut mounted on said lead screw, said second end of said flow restriction element coupled to said lead nut and, means external to said housing couplable to said seal to rotate said seal and thereby vary the axial insertion length of said flow restriction element by linear movement of said lead nut on said lead screw.

8. The infusion system of claim 1, wherein said outlet conduit comprises a rigid member connected at each end to a rigid coupling, said flow restriction element inserted into said conduit through one of said rigid couplings and seal means through which said flow restriction element passes in said coupling.

9. The infusion system of claim 1, further comprising an outlet catheter in fluid communication with said outlet conduit, an auxiliary infusion chamber separated from said constant pressure reservoir and having a penetrable self-sealing septum, said auxiliary infusion chamber coupled to said outlet catheter to provide a flow path to an infusion site without fluid from said constant pressure reservoir passing through said auxiliary infusion chamber.

10. The infusion system of claim 9, wherein said outlet catheter comprises a double lumen catheter having one flow path from said auxiliary chamber and a second flow path from said constant pressure reservoir.

11. The infusion system of claim 10, further comprising a second auxiliary chamber, a T-connector providing a fluid coupling to said second flow path without fluid from said constant pressure reservoir passing through said second auxiliary chamber.

* * * * *